(12) United States Patent
Aberg et al.

(10) Patent No.: US 8,778,971 B2
(45) Date of Patent: Jul. 15, 2014

(54) MEDICINAL TREATMENT OF DERMAL DISEASES IN COMPANION ANIMALS

(71) Applicants: A.K. Gunnar Aberg, Sarasota, FL (US); Vincent B. Ciofalo, Branford, CT (US)

(72) Inventors: A.K. Gunnar Aberg, Sarasota, FL (US); Vincent B. Ciofalo, Branford, CT (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 14/025,302

(22) Filed: Sep. 12, 2013

(65) Prior Publication Data

US 2014/0113936 A1    Apr. 24, 2014

Related U.S. Application Data

(63) Continuation-in-part of application No. 13/739,090, filed on Jan. 11, 2013, now Pat. No. 8,557,846.

(60) Provisional application No. 61/717,240, filed on Oct. 23, 2012.

(51) Int. Cl.
*A61K 31/4535*    (2006.01)

(52) U.S. Cl.
USPC ......................................................... 514/324

(58) Field of Classification Search
None
See application file for complete search history.

(56) References Cited

U.S. PATENT DOCUMENTS

| | | | |
|---|---|---|---|
| 3,682,930 | A | 8/1972 | Bourquin et al. |
| 4,659,716 | A | 4/1987 | Villani et al. |
| 5,595,997 | A | 1/1997 | Aberg et al. |
| 6,207,683 | B1 | 3/2001 | Aberg et al. |
| 6,207,684 | B1 | 3/2001 | Aberg |
| 7,226,934 | B1 | 6/2007 | Aberg et al. |
| 7,557,128 | B2 | 7/2009 | Aberg et al. |
| 2007/0282008 | A1 | 12/2007 | Mason |
| 2010/0105734 | A1 | 4/2010 | Aberg et al. |
| 2010/0130550 | A1 | 5/2010 | Aberg et al. |
| 2012/0076872 | A1 | 3/2012 | Hsu |

FOREIGN PATENT DOCUMENTS

WO    0119367 A1    3/2001

OTHER PUBLICATIONS

U.S. Appl. No. 13/960,114, filed Aug. 6, 2013; "Methods of Treating Pruritic Conditions Mediated Through Histamine H-4 Receptors".
Potenzieri, et al.; "Basic mechanisms of Itch"; Clin Exp allergy; 42(1); pp. 8-19; (2012).
Robbach et al.; "The Histamine H4 Receptor as a New Target for Treatment of Canine Inflammatory Skin Diseases"; Veterinary Dermatology; 20; pp. 555-561; (2009).
U.S. Appl. No. 10/069,663, filed Nov. 29, 2006; 1.132 Declaration of A.K. Gunnar Aberg, filed Dec. 14, 2006; 3 pages.
U.S. Appl. No. 13/739,090, filed Jan. 11, 2013; A.K. Gunnar Abert; Medicinal Treatment of Dermal Diseases in Dogs.
U.S. Appl. No. 13/739,090, filed Jan. 11, 2013 NonFinal Office Action Mailed May 3, 2013.
Carlotti, D. N., "*Malassezia dermatitis* in the Dog": WSAVA World Congress, Vancouver. Available at: http://www.triton-vet.com/pub%20tritohexidin%20plus3.pdf, 2001.
DeBoer et al.; "The ACVD Task Force on Canine *Atopic dermatitis* (XII): The Relationship of Cutaneous Infections to the Pathogenesis and Clinical Course of Canine *Atopic dermatitis*"; Vererinary Immunology and Immunopathology; 81; pp. 239-249; (2001).
Hiller et al.; "The ACVD Task Force on Canine *Atopic dermatitis* (I): Incidence and Prevalence"; Veterinary Immunology and Immunopathology; 81; pp. 147-151; (2001).
"U.S. Pet Ownership Statistocs"; by The Humane Society of the United States; www.humanesociety.org/issues/pet_overpopulation/facts/pet_ownership_statistics.html; 2 pages; printed Dec. 31, 2012.
Kennedy, G.R.; "Metabolism and Pharmacokinetics of Ketotifen in Children"; Research and Clinical Forums; 4; pp. 17-20; (1982).
Le Bigot et al.; "Metabolism of Ketotifen by Human Liver Microsomes_In Vitro Characterization of a Tertiary Amine Glucuronidation"; Drug Metabolism and Disposition; 11(6); pp. 585-589; (1983).
Maclay et al.; "Postmarketing Surveillance: Practical Experience With Ketotifen"; British Medical Journal; 288; pp. 911-914 (1984).
Nakashima et al.; "Fungus as an Exacerbating Factor of *Atopic dermatitis*, and Control of Fungi for the Remission of the Disease"; in *Atopic dermatitis*—Disease Etiology and Clinical Management; Ed. J. Esparza-Gordillo; ISBN: 978-953--51-0110-9; pp. 141-158 (2012).
Nolte et al.; "Inhibition of Basophil Histamine Release by Methotrexate"; Agents Actions; 23; pp. 173-176; (1988) Abstract.
Prowse, Keith; "Ketotifen in Adult Asthma"; British Medical Journal; 280; p. 646; (1980).
Roquet et al.; "Effects of Loratadine on Anti-IgE-Induced Inflammation, Histamine Release, and Leukocyte Recruitment in Skin of *Atopics*"; Allergy; 50(5); pp. 414-420; Abstract Only; (1995).
Ruben, Dawn; Diphenhydramine (Benadryl(R)); www.petplace.com/drug-library/diphenhydramine-benadryl/page1.aspx; 2 pages; printed Oct. 16, 2012.
Tonelli et al.; "A Bio-assay for the Concomitant Assessment of the Antiphlogistic and Thymolytic Activities of Topically Applied Corticoids"; Endocrinology; 77; pp. 625-634; (1964).
Wauquier et al.; "Further Studies on the Distinctive Sleep-Wakefulness Profiles of Antihistamines (Astemizole, Ketotifen, Terfenadine) in Dogs"; Drug Development Research; 4; pp. 617-625; (1984).
Dogs with *Atopic determatitis*: Causes, Diagnosis, and Treatment; from WebMD http://pets.webmd.com/dogs/dogs-atopic-dermatitis-causes-diagnosis-treatment; 3 pages; printed Dec. 31, 2012.
Dog Skin Disorders by Wikipedia; 2 pages; http://en.wikipedia.org/wiki/Dog_skin_disorders; printed Oct. 15, 2012.
Breuer et al.; "Bacterial Infections and *Atopic dermatitis*"; Allergy; 5; pp. 1034-1041; (2001).
Brockow, et al.; "Effect of Gentian Violet, Corticosteroid and Tar Preparations in *Staphylococcus-aureus*-Colonized *Atopic eczema*"; Dermatology; 199; pp. 231-236; (1999).
Ketotifen (Systemic); Professional Drug Information, Drugs.com, updated Mar. 6, 2008, Mar. 17, 2008 and Mar. 12, 2008;, printed Jul. 13, 2013; 11 pages.
Zaditen; Novartis, Pharmaceutical Information, Product monograph, printed Jul. 16, 2013; 3 pages.
Thomas, Randall C.; "Proceeding of the North American Veterinary Conference, Canine *Atopic dermatitis*: Old and New Therapies"; pp. 285-288; (2005).
International Search Report and Written Opinion; International Application No. PCT/US13/65847; International Filing Date Oct. 21, 2013; Date of Mailing Jan. 14, 2014; 16 pages.

*Primary Examiner* — Savitha Rao
*Assistant Examiner* — Gregg Polansky
(74) *Attorney, Agent, or Firm* — Cantor Colburn LLP

(57) ABSTRACT

The methods disclosed herein relate to the treatment of skin infections in dogs, by administering a therapeutically effective amount of norketotifen. Therapeutic antimicrobial activity of norketotifen against *Malassezia* sp. is described.

6 Claims, No Drawings

MEDICINAL TREATMENT OF DERMAL DISEASES IN COMPANION ANIMALS

CROSS-REFERENCE TO RELATED APPLICATIONS

This application is a continuation in part of U.S. application Ser. No. 13/739,090, filed on Jan. 11, 2013, which claims priority from U.S. Provisional Application Ser. No. 61/717,240 filed on Oct. 23, 2012, the disclosures of which are hereby incorporated by reference.

TECHNICAL FIELD

The embodiments disclosed herein relate to methods for treatment of inflammatory, infectious, and allergic dermal diseases in dogs while avoiding side effects that are commonly associated with anti-inflammatory antihistamines.

BACKGROUND

Ketotifen (Zaditen®, Zaditor®, Sandoz, Novartis) is a Generation-1 antihistamine that is mainly used for the treatment of allergic rhinitis. Ketotifen may be the most sedating of all marketed antihistamines and the unusually severe sedative side effects of ketotifen have limited the therapeutic usefulness of the drug. In the USA, ketotifen is only used as eye drops (Zaditor®, Novartis) to alleviate the symptoms of allergic conjunctivitis in humans and does not cause sedation due to the extremely low systemic concentrations of the drug after local administration to the eyes.

Norketotifen, an active metabolite of ketotifen, is an achiral molecule, but has two atropisomers, S-norketotifen and R-norketotifen, as has previously been described in U.S. Pat. Nos. 7,226,934 and 7,557,128. As explained in U.S. Pat. Nos. 7,226,934 and 7,557,128, norketotifen also has a significant sedation effect when studied in the art-accepted mouse model of sedation, and further, the sedative effects were attributed to the R-isomer. It was thus proposed that only the S-isomer could be administered without significant sedation effects.

Approximately 1500 fungi have been described, and some of them exist normally on the skin of various mammal species, including dogs, cats and humans. *Malassezia* species form a family of 6 to 10 lipolytic fungi. Overgrowth of *Malassezia* species causes toxic or immunological reactions and contributes to various dermal diseases and conditions, such as for example, adult seborrheic dermatitis, atopic dermatitis, dandruff, *Malassezia* dermatitis, *Malassezia* folliculitis, pityriasis versicolor, psoriasis, rosacea, seborrheic dermatitis and tinea. These disorders are typically treated with medication for the underlying condition in combination with an antifungal medication that can be administered orally or topically to the skin.

What is needed are methods of treating inflammatory and infectious dermal disorders without causing sedation or the much feared side effects of current medications for such diseases in dogs, which consist of corticosteroids and immunosuppressant drugs. Also needed are improved topical treatments for dermal disorders.

SUMMARY

In one aspect, a method for treating pruritic and/or inflammatory dermal disorders in a dog in need of such treatment comprises administering to the dog in need a therapeutically effective amount of norketotifen or a pharmaceutically acceptable salt thereof, wherein the therapeutically effective amount does not produce sedative side effects upon administration to the dog. In further embodiments, norketotifen does not cause the side effects of long-term administration of corticosteroids or the side effects of immunosuppressant drugs.

In another aspect, a method for reducing sedative side effects in the treatment of pruritic and/or inflammatory dermal disorders in a dog in need of such treatment comprises administering to the dog in need a therapeutically effective amount of norketotifen or a pharmaceutically acceptable salt thereof that does not produce sedative side effects upon administration to the dog.

A method of treating skin infections in a dog or cat, comprising administering to the dog or cat with a skin infection a topical formulation comprising a therapeutically effective amount of norketotifen or a salt or isomer thereof and a pharmaceutically acceptable excipient.

In another aspect, a method of treating a skin infection in a dog or cat comprises orally administering to the dog or cat with a skin infection a therapeutically effective amount of RS-norketotifen or a pharmaceutically acceptable salt thereof.

DETAILED DESCRIPTION

The methods disclosed herein relate to the treatment of pruritic, inflammatory, and/or infectious dermal disorders, such as for example atopic dermatitis, in companion animals such as dogs and cats, by administering the anti-inflammatory, anti-allergic, and anti-microbial compound, norketotifen and pharmaceutically acceptable salts thereof. Prior to the present disclosure, the antimicrobial efficacy of norketotifen and the isomers thereof had not been reported. In certain aspects, administration is oral administration, topical administration, or a combination thereof.

It had previously been found and described that both ketotifen and norketotifen express sedative activity, and were therefore not considered to be useful as oral medications for the treatment of chronic diseases, such as for example, atopic dermatitis in dogs. Sedation was determined using a mouse model that has previously been used successfully in the development of non-sedating antihistamines, such as loratadine (Claritin®, Schering) and desloratadine (Clarinex®, Schering). It was therefore believed that the mouse model had relevance for evaluating the clinical use of the current benzocycloheptathiophene compound that has potent antihistaminic activities. The mouse model clearly demonstrated the sedative effects norketotifen and R-norketotifen.

It has now surprisingly been found that racemic norketotifen is completely free from sedative effects when orally administered to dogs, even after administration of high doses of the compound.

It has further been unexpectedly discovered that norketotifen and its isomers have antimicrobial activity and can be used to inhibit the growth of microorganisms such as fungi and bacteria including *Malassezia* sp, *Candida albicans*, and *Staphylococcus aureus*. Thus, in one aspect, disclosed herein is a method of treating skin infections in a dog comprising administering to the skin (e.g., an infected skin lesion and adjacent areas) of the dog a topical formulation comprising a therapeutically effective amount of norketotifen or a salt or isomer thereof and a pharmaceutically acceptable excipient. Skin infections can also be treated by oral administration of norketotifen.

In one aspect, the active compound is racemic norketotifen, herein often called RS-norketotifen or just norketotifen. Norketotifen is an achiral molecule, but has two isomers, S-norketotifen and R-norketotifen, as has previously been described in U.S. Pat. Nos. 7,226,934 and 7,557,128. Norketotifen is particularly useful for both oral and topical administration.

Chemically, norketotifen is (RS)-4-(piperidylidene)-9,10-dihydro-4H-benzo-(4,5)-cyclohepta-(1,2-b) thiophene-10-one. The prefix (RS) can optionally be excluded when referring to racemic norketotifen.

Norketotifen is a metabolite of ketotifen (4-(1-methyl-4-piperidyline)-4H-benzo(4,5)-cyclohepta-(1,2-b) thiophene-10-one). Ketotifen may be the most sedating of all marketed antihistamines and the unusually severe sedative side effects of ketotifen has limited the therapeutic usefulness of the drug, particularly when orally administered in the treatment of atopic dermatitis in dogs, since very high doses such as 0.5 to 20 mg/kg body weight once or twice daily have to be used in dogs.

KETOTIFEN

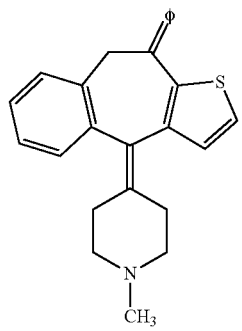

The metabolite norketotifen is formed by demethylation of ketotifen in the liver of most mammals:

NORKETOTIFEN

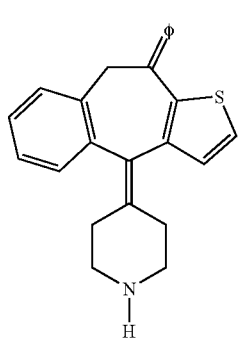

Norketotifen can be made from methods known in the art, as described in U.S. Pat. No. 3,682,930, the disclosure of which is hereby incorporated by reference for its teaching of the synthesis of norketotifen.

Except for U.S. Pat. Nos. 7,226,934 and 7,557,128, no publications are known that describe the pharmacodynamic activities of RS-norketotifen. U.S. Patent Publications 2010/0105734 and 2010/0130550 describe the effects of RS-norketotifen when used as eye drops for ocular conjunctivitis and xerophthalmia in humans.

Certain embodiments disclosed herein provide for the oral administration of the racemic form of norketotifen or pharmaceutically acceptable acid addition salts of the compound to dogs in need thereof. Norketotifen is ideally suited for the treatment of atopic dermatitis (AD) in dogs, since this compound, has potent anti-inflammatory and antipruritic effects, and has now, surprisingly, been found to be completely free from sedative side effects and to have antimicrobial effects of significant importance in dogs. In a specific embodiment, the norketotifen is racemic norketotifen.

Dogs may suffer from various types of skin diseases, which are most often inflammatory, pruritic and infectious disorders. Examples are *Malassezia* dermatitis (causing allergic reactions and expressing mild to severe pruritus), atopic dermatitis (expressing inflammation and severe pruritus), hot spot (expressing inflammation and severe pruritus) and seborrheic dermatitis (expressing inflammation and pruritus).

Atopic (allergic) dermatitis in dogs can be caused by various allergens, such as for example food allergens, fleas, bacteria, fungi or contact allergens. What may start as seasonal atopic dermatitis often becomes a year-round problem as the dog ages and the skin becomes increasingly sensitive to additional allergens.

Because of the potent anti-inflammatory, antipruritic, and antimicrobial activities of norketotifen, this substance may be of medicinal value to dogs suffering from a variety of dermal diseases. Of particular importance is the use of norketotifen in dogs suffering from atopic dermatitis, which is a common disease in dogs and is believed to affect between 10 and 20 percent of the 78 million owned dogs in the United States.

In one embodiment, a method for reducing sedative side effects in the treatment of pruritic and/or inflammatory dermal disorders in a dog in need of such treatment comprises orally administering to the dog in need a therapeutically effective amount of norketotifen or a pharmaceutically acceptable salt thereof that does not produce sedative side effects upon administration to the dog. In one embodiment, treatment is chronic, subchronic, or acute, specifically chronic. As used herein chronic administration is three or more consecutive days of administration, specifically six or more consecutive days of administration. Acute refers to a single administration. Subchronic refers to less than 3 consecutive days of administration. In a specific embodiment, the norketotifen is racemic norketotifen.

In another aspect, disclosed herein is a method of treating a dog in need of treatment for a skin infection comprising administering to the skin (e.g., to an infected skin lesion and the infected adjacent non-lesion skin on the dog) a topical formulation comprising a therapeutically effective amount of norketotifen or a salt or isomer thereof and a pharmaceutically acceptable excipient. Oral administration can be used in addition to or as an alternative to topical administration. Both bacteria and fungi can be found in skin lesions and in areas of the adjacent to the lesions on dogs and cats suffering from atopic dermatitis. *Staphylococcus aureus* bacterial infections are common in human and canine patients with AD and very prevalent in lesions and in normal skin adjacent to the lesions. *S. aureus* is believed to be causative for some of the manifestations of Atopic Dermatitis since a toxin that is produced by the bacteria (staphylococcus enterotoxin B) has been found to induce both induration and erythema of the skin of healthy human volunteers and volunteers with atopic dermatitis.

*Candida albicans* dermal fungal infections are common among human and canine patients with Atopic Dermatitis and clinical studies have linked the presence of anti-*Candida albicans* antibodies in the blood with the clinical condition of atopic dermatitis.

*Malassezia* sp dermal fungus and in particular *Malassezia pachydermatis* is probably the most common microorganism in infected skin lesions in canine and feline atopic dermatitis, and is also known to cause exacerbation of the disease and to cause intense pruritus. *M. globulosa, M. sympodialis* and *M.*

*furfur* cause Tinea versicolor, which is a chronic superficial fungal infection in humans with a prevalence of 30-40 percent in tropical areas. *M. furfur* and possibly other *Malassezia* species, can induce the overproduction of molecules (such as TGF-beta-1) involved in cell migration and hyperproplification, thereby favoring the exacerbation of psoriasis. *M. pachydermatis* is very common in dogs with atopic dermatitis and is considered as causative for *Malassezia* dermatitis in dogs and possibly also for atopic dermatitis in dogs.

When the skin of a dog is cut or wounded, there is an increased risk of skin infection. In addition, underlying conditions such as allergies and invasion by parasites cause inflammation and scratching, leading to open lesions which can become infected. Skin infections are evidenced by lesions, pustules, discharge, scaling, crustiness and in some cases hair loss at the site of the infection.

Bacterial skin infections in dogs can result from an underlying immune disorder, allergies, hormonal disease, liver disease and kidney disease, for example. Inflammation and scratching break down dermal barriers leading to infection.

A particular problem in dogs is hot spots, areas of inflamed skin that come on quickly in dogs. The dogs focus on these sites and licking and chewing rapidly lead to worsening of the site and infection. Topical treatments typically include antibiotics to treat the infection and corticosteroids to treat the inflammation. Advantageously, norketotifen has both antimicrobial and anti-inflammatory properties.

Infected skin lesions can be readily identified by visual inspection and/or skin cytology of the lesions. Cells from the lesion are stained and then examined under a microscope. Both fungi and bacteria can be identified in this manner by the different stains as well as the shape of the cells. In addition, the underlying causative microorganism can be identified by cell culture techniques.

Cats, in addition to dogs, suffer from infected skin lesions and hot spots, due to underlying allergic conditions or parasite infections, for example. Topical treatment of infected skin lesions in cats may be treated similarly to dogs.

The embodiments disclosed herein also provide pharmaceutical compositions, which comprise the compound of the invention, formulated together with one or more pharmaceutically acceptable carriers. The pharmaceutical compositions may be specially formulated for oral administration, parenteral administration, or topical administration. The term "parenteral" administration includes intravenous, intraarterial, intramuscular, intraperitoneal, or subcutaneous administration forms.

Pharmaceutical compositions for oral administration of solid dosage forms include capsules and tablets. In solid dosage forms, the active compound may be mixed with one or more pharmaceutically acceptable excipients or carriers (such as for example sodium citrate, dicalcium phosphate), fillers or extenders (such as for example starch, lactose, sucrose, glucose, mannitol, silicic acid), binders (such as for example alginates, carboxymethylcellulose, gelatin, polyvinylpyrrolidone, sucrose, acacia), humectants (such as for example glycerol), solution retarding agents (such as for example paraffin), disintegrating agents (such as for example agar-agar, calcium carbonate, starch, alginic acid, silicates, sodium carbonate), absorption accelerators (such as for example quaternary ammonium compounds), wetting agents (such as for example cetyl alcohol, glycerol monostearate), absorbents (such as for example kaolin, bentonite clay), lubricating agents (such as for example talc, calcium stearate, magnesium stearate, polyethylene glycols, sodium lauryl sulfate), and/or other excipients, such as for example buffering agents.

Liquid dosage forms for oral administration include pharmaceutically acceptable emulsions, solutions, suspensions, syrups and elixirs. The liquid dosage form may also contain commonly known diluents (such as for example water, other solvents, solubilizing agents), emulsifiers (such as for example ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof.)

The oral compositions may also include other excipients as known to those skilled in the art. The drug can also be administered orally as dog treats.

Pharmaceutical compositions for parenteral injections include pharmaceutically acceptable sterile solutions, dispersions, suspensions, emulsions and sterile powders for reconstitution into sterile injectable solutions or dispersions prior to use. Various carriers, diluents, solvents and vehicles may be used. Fluidity can be maintained by use of coating material such as lecithin, by restricting particle size and by use of surfactants.

Parenteral compositions may also contain excipients such as for example preservatives, wetting agents, emulsifying agents, dispersing agents, isotonic agents, and/or absorption-delaying agents. Absorption-prolonging or absorption-slowing effects may be achieved by injecting a crystalline or amorphous suspension with low water solubility.

Pharmaceutical compositions for topical application include, for example, pharmaceutically acceptable solutions, emulsions, creams and ointments, containing 0.1 percent to 10 percent of norketotifen or a pharmaceutically acceptable salt thereof, which may be applied one or more times daily. The topical formulations will also contain one or more pharmaceutically acceptable excipients.

A large number of excipients have now been tested for compatibility with norketotifen, and excipients have been identified that are compatible with norketotifen. Examples of compatible excipients, are antioxidants, such as sulfites or ascorbates, at concentrations of about 0.05 percent to about 3 percent, specifically about 0.1 percent to about 0.25 percent by weight; buffering agents, such as for, example, phosphates, borates, citrates and acetates, at concentrations of about 0.01 percent to about 4 percent by weight; chelating agents, such as, for example, edetate or chitosan polysaccharides, at concentrations of about 0.01 percent to about 10 percent, specifically about 0.01 percent to about 2.0 percent by weight; emollients, such as, for example, glycerin or propylene glycol, at concentrations of about 0.1 percent to about 10 percent, specifically about 0.1 percent to about 2.0 percent by weight; gelling agents, such as, for example, alginates or gelling polymers, at concentrations of about 0.05 percent to about 10 percent, specifically about 0.1 percent to about 2.5 percent by weight; in situ gelling agents, such as alginate/HPMC (hydroxypropyl methylcellulose) or polyacrylic acid (Carbopol)/HPMC, at concentrations of about 0.5 percent to about 10 percent, specifically about 0.1 percent to about 2.5 percent by weight; humectants, such as, for example, polyethylene glycol or propylene glycol, at concentrations of about 0.05 percent to about 10 percent by weight; stabilizers, such as methylcellulose or chitosan, at concentrations of about 0.05 percent to about 4 percent, specifically about 0.05 percent to about 2.0 percent by weight; combined stabilizer/solubilizers, such as for example α-, β- or γ-cyclodextrin, at concentrations of about 0.1 percent to about 20 percent by weight; surfactants, such as, for example glyceryl stearate or polyethoxylated castor oil, at concentrations of about 0.05 percent to about 4.0 percent, specifically about 0.1 percent to about 2.0 percent by weight; and viscosity-adjusting agents, such as, for example, methylcellulose or propylene glycol alginate, at concentrations of about 0.1 percent to about 10 percent, specifically about 2.0 percent to about 5.0 percent by weight.

Numerous compositions using said excipients have been prepared and tested using an HPLC method for the determination of concentrations of norketotifen that has been developed for this purpose.

The actual dosage levels of active ingredients in the pharmaceutical compositions disclosed herein may be varied so as to obtain the desired therapeutic effect. Thus the amount of drug used varies and will depend on factors such as the administration form, the severity of the disease, the frequency of dosing, and other circumstances (such as general health, age, etc.) known to the caretaker of the dog and the caring veterinarian.

The therapeutically effective oral doses of norketotifen useful for treating dogs with atopic dermatitis (AD) will be determined by the caring veterinarian and are generally higher than doses used for human patients with AD, specifically 0.5 mg/kg to 20 mg/kg bodyweight (calculated as free base) and more specifically 4 mg/kg to 16 mg/kg (calculated as free base), dosed orally as the free base or as a salt, such as for example the hydrochloride or mesylate salts or the hydrogen fumarate salt, once, twice or more times daily. In one embodiment, the treatment is once daily dosing. The therapeutically effective dose may be administered less than once daily, such as for example two to six times weekly, as determined by the caretaker of the animal or the caring veterinarian. Typically, after therapeutic efficacy has been established, the dosing of norketotifen may be decreased from daily dosing to dosing two to six times weekly.

The actual dosage levels of norketotifen in the topical compositions disclosed herein may be from 0.1 percent to 20 percent, preferably 0.1 percent to 10 percent, by weight, but may be varied so as to obtain the desired therapeutic effect.

When used for treatment of dermal disorders, other than atopic dermatitis in dogs, norketotifen can be used in the same doses or in similar doses as described herein for the treatment of atopic dermatitis in dogs. As always, the dose to an individual dog will be modified according to the weight of the animal, the severity of the disease and other circumstances known to the caretaker and the caring veterinarian.

The frequency of dosing and the amount of drug being administered to a particular dog will be determined by the caretaker or a veterinarian and will be based on various clinical factors, such as for example the weight and age of the dog and the severity of the disease of the dog.

The embodiments disclosed herein provide methods for treatment of immunologic, inflammatory, pruritic and microbial skin disorders in dogs, while avoiding the sedating side effects of ketotifen. These methods comprise administering to the canine in need of such treatment, effective amounts of norketotifen or a pharmaceutically acceptable salt thereof, at a dosing frequency to be determined for the individual dog by the caretaker or the caring veterinarian. In one embodiment, dosing frequency is once daily.

In addition to the use of norketotifen as single-drug medication in dogs, embodiments disclosed herein also provide methods for co-administration of norketotifen with at least one drug of the following classes: insecticidal agents, antibacterial agents, antiviral agents, vitamin D or vitamin D analogs, corticosteroids, cyclooxygenase inhibitors, leukotriene antagonists, lipoxygenase inhibitors, inhibitors of one or more cytokines, and immunomodulators, such as for example cyclosporine. The co-administration may be temporary or may be chronically used in the patient dog. The co-administered drug can be administered to the dog separately or can be co-formulated with norketotifen for oral, parenteral or dermal administration.

Of specific importance is co-administration of norketotifen with an anti-inflammatory corticosteroid, since onset time of the therapeutic activity of norketotifen in dogs suffering from atopic dermatitis may be shortened by said co-administration. For this purpose, norketotifen can be combined with a corticosteroid for the first one to four weeks of therapy. The dose of the corticosteroid depends on the potency of said corticosteroid. High-potency or mid-potency corticosteroids are preferred. As an example, if the mid-potency corticosteroid prednisone, or its metabolite prednisolone, is used in combination with norketotifen, the dose of said corticosteroid is 0.1 to 5.0 mg/kg bodyweight/day and can be combined with an oral dose of norketotifen that is from 0.5 mg/kg bodyweight to 20 mg/kg bodyweight (dosed once or twice daily and calculated as free base). The combination treatment of norketotifen and a corticosteroid like prednisone or prednisolone can be administered to dogs suffering from atopic dermatitis. The combination of norketotifen and a corticosteroid can be administered in double dose for the first one to seven days of therapy. Following the initial treatment of the dog with a combination of norketotifen and a corticosteroid, the continued treatment will consist of norketotifen monotherapy, as described above.

In one embodiment, norketotifen is initially orally or topically co-administered for one to four weeks of therapy with a corticosteroid in a therapeutically active dose, thereafter followed by monotherapy, wherein norketotifen or a pharmaceutically acceptable salt thereof, when orally administered, is administered in an amount of 0.5 mg/kg to 20 mg/kg, dosed once or twice daily and calculated as free base.

Those skilled in the art of pharmacology will realize that corticosteroid-sparing doses will be obtained by co-administration of norketotifen at normal oral daily doses of between 0.5 mg/kg bodyweight and 20 mg/kg bodyweight dosed once or twice daily and calculated as free base with doses of corticosteroids that are lower than said doses when the corticosteroids are administered as monotherapy. Thus, in dogs suffering from atopic dermatitis, it will be possible to reduce the common therapeutic doses of corticosteroids by 50 percent or more by co-administration of norketotifen at doses ranging from 0.5 mg/kg to 20 mg/kg dosed once or twice daily and calculated as free base. A regular dose of prednisone to dogs suffering from atopic dermatitis depends on the size and age of the dog and the severity of the disease and may range from 1.0 mg/kg bodyweight/day to 2 mg/kg bodyweight, or the dose may be even higher. During co-administration with norketotifen the doses of prednisone may be decreased to 0.5 mg/kg bodyweight/day to 1 mg/kg bodyweight, or the doses of the steroid may be reduced even further, which reductions are herein considered to be half the regular dose of said steroid.

When used for the treatment of dermal disorders other than atopic dermatitis in dogs, co-administration of norketotifen and a corticosteroid, such as for example prednisone, will result in a corticosteroid-sparing treatment. The same doses of norketotifen and the corticosteroid as described herein for corticosteroid-sparing treatment of atopic dermatitis, can be used. As always, the dose to an individual dog will have to be modified according to the weight of the animal, the severity of the disease and other circumstances known to the caretaker and the caring veterinarian.

Similarly, it will be possible to reduce the doses of an immunosuppressant drug, such as for example cyclosporine with co-administration of norketotifen. Thus, in dogs suffering from atopic dermatitis, it will be possible to reduce common therapeutic doses of an immunosuppressant drug by 50 percent or more by co-administration of norketotifen at normal oral doses, which are ranging from 0.5 mg/kg bodyweight to 20 mg/kg bodyweight, once or twice daily, thereby reducing the potentially very serious side effect of the immunosuppressant drug. As an example, the regular dose of cyclosporine to dogs with atopic dermatitis is 5 mg/kilogram body weight/day until therapeutic efficacy is obtained and thereafter the dose may be decreased to a level where therapeutic activity is maintained in the individual dog. During co-administration with a normal dose of norketotifen, the initial dose of the immunosuppressant drug cyclosporine may be decreased to a range from 1 mg/kilogram bodyweight/day to 3 mg/kilogram bodyweight/day, which is herein called "half the regular dose". The dose of the immunosuppressant drug can be further reduced by dosing the drug every other day, or even more seldom, which is herein called a "further reduced regular dose" of the immunosuppressant. Examples of immunosuppressant drugs are cyclosporine (Atopica®, Novartis), pimecrolimus (Elidel®, Novartis, Meda) and tacrolimus (Protopic®, Astellas Pharma). Immunosuppressant drugs are also called immunomodulating drugs or calcineurin inhibitors.

When used for treatment of other dermal disorders than atopic dermatitis in dogs, co-administration of norketotifen and an immunomodulating drug, such as for example cyclosporine, will use the same doses as described herein for the treatment of atopic dermatitis. As always, the dose to an individual dog will have to be modified according to the drug used, the weight of the animal, the severity of the disease and other circumstances known to the caretaker and the caring veterinarian.

In one aspect, topical drug administration of norketotifen is combined with oral administration of norketotifen. For example, a dog suffering from atopic dermatitis may have patches of skin that become infected by the fungus *Malassezia*, due for example, to excessive scratching and licking of the skin. By combining systemic (oral) administration and local (topical) administration, both the skin infection and the underlying dermatitis can be treated simultaneously. Advantageously, neither the oral nor the dermal administration of norketotifen will be expected to produce sedation in the animal.

EXAMPLES

Example 1

Antihistaminic Activity In Vitro $H_1$ receptor binding studies were conducted utilizing human recombinant receptors. In the studies shown herein, affinities of the test compounds for histamine $H_1$-receptors were assessed using a binding assay, where [$^3$H]pyrilamine was used as the ligand and the test compounds were used at increasing concentrations. The specific binding of the radioactive ligand to the receptor was defined as the difference between total binding and nonspecific binding, determined in the presence of excess unlabeled ligand. $IC_{50}$ values (the concentration that inhibits 50% of specific binding of the ligand) are determined by non-linear regression analysis of the competition curves. The results are shown in Table 1.

TABLE 1

Antihistaminic activity in vitro

| ANTIHISTAMINE | H-1/IC50 (nM) |
|---|---|
| KETOTIFEN | 2.3 |
| NORKETOTIFEN | 11 |
| LORATADINE (Claritin ®) | 1,500 |
| DESLORATADINE (Clarinex ®) | 16 |
| DIPHENHYDRAMINE (Benadryl ®) | 84 |

Ketotifen is probably the most potent antihistaminic compound ever to be approved as a drug for human use. Norketotifen has less affinity for the histamine-1 receptors than ketotifen, but is more potent than the three reference compounds. Loratadine is a poorly active prodrug and is metabolized in the liver to desloratadine.

Example 2

Antihistaminic Activity In Vivo

Male rats (150-200 g) were fasted overnight and twelve hours after dorsal depilation, the animals were orally pretreated with the test compound(s). Four dorsal test areas were marked with permanent ink, carefully avoiding the area closest to the spine. Sixty minutes after the dosing with the test compound, two intradermal injections of histamine (50 µL; 1.0 mg/ml of histamine di-HCl) were performed, one on each side on the back of the animal. Two intradermal injections of the vehicle for the histamine solution were also performed. Evans blue dye (20 mg/kg) was injected intravenously one minute prior to the intra-dermal injections of histamine and the histamine vehicle. Twenty minutes were allowed for the wheal response to fully develop, whereupon the animals were euthanized and the dorsal skin with the intradermal wheals were deflected. The blue spotted areas were measured in square millimeters and the duplicate wheal areas were averaged. In vehicle-treated animals, the wheal area, on average, was increased by histamine by 94 and 82 $mm^2$ for the vehicles used during the norketotifen and ketotifen experiments, respectively. The inhibition was calculated in percent difference from said baseline values. The results are shown in Table 2.

TABLE 2

Antihistaminic activity in vivo

| Test compound Dose (mg/kg) | Histamine ($mm^2$) | Saline ($mm^2$) | Histamine effect ($mm^2$) | Inhibition (%) |
|---|---|---|---|---|
| Vehicle* | 116 ± 5 | 22 ± 1 | 94 | — |
| Vehicle** | 107 ± 4 | 25 ± 1 | 82 | — |
| Ketotifen; 1.0 | 68 ± 6 | 21 ± 2 | 47 | 43 |
| Ketotifen; 10 | 24 ± 2 | 22 ± 3 | 2 | 98 |
| Norketotifen; 1.0 | 114 ± 8 | 22 ± 1 | 92 | 2 |
| Norketotifen; 10 | 39 ± 2 | 22 ± 1 | 17 | 82 |
| Norketotifen; 50 | 10 ± 1 | 12 ± 1 | 0 | 100 |
| DPH; 10*** | | | | 31 |

*Vehicle for norketotifen expts
**Vehicle for ketotifen expts
***DPH = diphenhydramine (Benadryl ®)

When plotted, ketotifen was found to be 2 to 3 times more potent than norketotifen as an antihistamine in these in vivo studies. Norketotifen was significantly more potent than diphenhydramine.

Example 3

Anti-Inflammatory Effects In Vitro

In these studies, histamine was the marker compound for inflammatory mediators that are released from mast cells and other pro-inflammatory cells in patients with atopic inflammatory diseases. The inhibition of stimulated histamine release from human leukocytes (buffy coat) by test articles was studied. Leukocytes were obtained from healthy volunteers and histamine release was induced by incubation (20 min/37° C.) with the calcium ionophore A23187 (5 µM) in the presence or absence of a test article. Histamine was analyzed by enzyme-immune assays, using commercially available kits and a microplate reader (MRX, Dynatech). The test articles were evaluated, in duplicate, at five concentrations. The results are shown in Table 3.

TABLE 3

Inhibition of inflammatory mediator (histamine) release; IC50 (µM)

| Test article | IC50 (µM) |
|---|---|
| Ketotifen | 91 |
| Norketotifen | 9.2 |

Norketotifen was approximately 10 times more potent than ketotifen as an inhibitor of histamine release from pro-inflammatory cells.

Example 4

Anti-Inflammatory Effects In Vivo: Systemic Administration

In order to investigate the effects of systemic administration of the test compounds in dermal inflammation, a *croton* oil model was used as is known in the art. This test consists of topical application of 20 µl of 1.0% *croton* oil to each ear of male mice, weighing 28-32 g. The weight of untreated ears of these animals is 30-32 mg. Application of the *croton* oil results in an inflammatory response. The weight of *croton* oil-treated ears was determined and the percent increase in ear weight is calculated. Test articles were dosed systemically (ip).

The effects of 10 mg/kg of RS-ketotifen and RS-norketotifen at 90 and 120 minutes after administration of test articles are shown in the following table. All results represent mean ear weights (±S.E.M.) from 10 ears. The results are shown in Table 4.

TABLE 4

Anti-inflammatory effects *in vivo*

| Test Article | Average Ear weight (mg) ±SEM | |
|---|---|---|
| | 90 min | 120 min |
| Control | 48 ± 2 | 51 ± 2 |
| Ketotifen | 37 ± 1 | 42 ± 1 |
| Norketotifen | 34 ± 1 | 40 ± 1 |

Both test compounds demonstrated dermal anti-inflammatory effects. All or part of the anti-inflammatory effect of ketotifen is assumed to be due to norketotifen that is formed as a metabolite of ketotifen in the rodents.

Example 5

Sedative Effects in Mice

The sedation study in mice has previously been used by Schering in the loratadine project (U.S. Pat. No. 4,659,716, 1987) and by Sepracor in the desloratadine project (U.S. Pat. No. 5,595,997), which patents are hereby included by reference for their disclosure of sedation studies. In short, physostigmine (1.0 mg/kg to 2.0 mg/kg, s.c.) generally results in 100% lethality when given to groups of mice (10 mice/group) transferred into a small volume of space. Mice administered a sedating drug prior to the physostigmine injection are protected from the stress and survive. In the present study, test compounds were given orally 60 minutes prior to physostigmine injection. The number of surviving (sedated) mice was counted 30 minutes after injection of the physostigmine dose. Results are shown from tests that were performed between the years 1997 and 2009 in Table 5.

TABLE 5

Sedative effects in mice

| | Oral dose (mg/kg) | Sedated animals |
|---|---|---|
| VEHICLE | — | 0/10 |
| NORKETOTIFEN | 83 | 3/10 |
| NORKETOTIFEN | 100 | 3/10 |
| NORKETOTIFEN | 150 | 3/10 |
| NORKETOTIFEN | 180 | 6/10 |
| S-NORKETOTIFEN | 100 | 0/10 |
| S-NORKETOTIFEN | 150 | 0/10 |
| R-NORKETOTIFEN | 100 | 3/10 |
| R-NORKETOTIFEN | 150 | 3/10 |
| KETOTIFEN (Zaditen ®; Gen-1) | 25 | 5/10 |
| KETOTIFEN (Zaditen ®; Gen-1) | 50 | 8/10 |
| KETOTIFEN (Zaditen ®; Gen-1) | 100 | 10/10 |
| CYPROHEPTADINE (Periactin ®; Gen-1) | 100 | 9/10 |
| PYRILAMINE (Mepyramine ®; Gen-1) | 100 | 8/10 |
| HYDROXYZINE (Atarax ®; Gen-1) | 100 | 9/10 |
| DIPHENHYDRAMINE (Benadryl ®; Gen-1) | 50 | 5/10 |
| DIPHENHYDRAMINE (Benadryl ®; Gen-1) | 100 | 8/10 |
| ASTEMIZOLE (Hismanal ®; Gen-2) | 100 | 1/10 |
| NORASTEMIZOLE (Soltara ™; Gen-2) | 100 | 0/10 |
| LORATADINE (Claritin ®; Gen-2) | 150 | 1/10 |
| DESLORATADINE (Clarinex ®; Gen-2) | 150 | 0/10 |
| TERFENADINE (Seldane ®; Gen-2) | 150 | 0/10 |
| FEXOFENADINE (Allegra ®; Gen-2) | 150 | 0/10 |

Gen-1 = Generation-1 (sedating antihistamines)
Gen-2 = Generation-2 (non-sedating antihistamines)

All registered Generation-1 antihistamines were sedating in mice and all registered Generation-2 antihistamines were free from sedation, using the physostigmine lethality test. Racemic norketotifen expressed sedative activity in this test system.

Example 6

Sedative Effects in Dogs

Sedation studies in dogs were performed according to a cross-over protocol, where the dogs were administered once daily the test articles orally at a dose of 20 mg/kg bodyweight that in a previous toxicology study was marginally toxic in dogs with equal plasma concentrations of R-norketotifen and S-norketotifen.

The test articles were administered in gelatin capsules and vehicle-capsules were empty. All dogs were healthy beagles (four males and two females), age 24-36 months, weighing 7.8-10.6 kg. The dogs were dosed at 9-10 AM and had been fasted overnight before dosing. There was a washout period of at least three days in all dogs between the tests. All assessments of sedation/sleepiness were made by a qualified (D.V.M.) scientist with extensive experience (>15 years) in studies with conscious laboratory dogs. The test articles were in the form of hydrogen fumarate salts.

It had previously been observed that dogs rarely express sedation in response to oral administration of benzocycloheptathiophene compounds on the first day of dosing and the dogs were therefore administered the test articles for three consecutive days. The results are shown in Table 6.

TABLE 6

Sedative effects in dogs

| Treatment | Frequency of sedation | | |
|---|---|---|---|
| (20 mg/kg/day) | DAY 1 | DAY 2 | DAY 3 |
| Ketotifen | 0/6 | 5/6 | 5/6 |
| Norketotifen | 0/6 | 0/6 | 0/6 |
| Vehicle | 0/6 | 0/6 | 0/6 |

The test results demonstrate that ketotifen causes sedation in dogs, which is not surprising, since diphenhydramine (Benadryl®) also causes sedation in dogs.

Surprisingly, norketotifen did not cause sedation in dogs, which is contrary to the results from earlier animal studies using the mouse physostigmine model, which test method has been considered to be of high predictive value. To our knowledge, this is the first study that has been performed to specifically study sedative side effects of norketotifen in dogs and it has now surprisingly been found that racemic norketotifen is completely free from sedative effects in this species.

The sedative effects of ketotifen have been reported from tests using the mouse physostigmine sedation tests. Sedative side effects of ketotifen, expressed as effect on the sleep pattern in dogs, have been published. Sedative side effects of norketotifen are reported herein and have been reported from tests using the physostigmine test method. To our knowledge, norketotifen has never been administered to dogs suffering from any disease, including atopic dermatitis.

Example 7

Toxicological Effects

Acute toxicological studies were performed in rats (Sprague-Dawley; M and F; 200-250 grams). The animal-sparing Up-and-Down Procedure (FDA, OECD) was used. Both oral and intravenous toxicity tests were performed.

The acute toxicity, expressed as estimated LD50 and calculated in mg/kg body weight of norketotifen and ketotifen are shown in Table 7. Both compounds were administered as hydrogen fumarate salts.

TABLE 7

| | Toxicological effects Acute toxicity (estimated LD50) mg/kg | |
|---|---|---|
| TEST SYSTEM | NORKETOTIFEN | KETOTIFEN |
| RAT; intravenous | 10-15 | 5-10 |
| RAT; oral | 1500-2000 | <300 |

Norketotifen is significantly less toxic than ketotifen after intravenous or oral administration.

Example 8

Anti-Inflammatory Effects In Vivo. Topical Drug Administration

In order to investigate the effects of topical administration of the test compounds in dermal inflammation, a modified *croton* oil model was used. About 10 mg of a cream containing 1.0% norketotifen or a vehicle cream was applied to both ears of mice for 30 minutes. The cream was then removed and a solution of 1% *croton* oil in 20 µl acetone was applied to both ears. After the acetone had dried (10 seconds), the cream containing the test article (or vehicle) was reapplied and the animals were returned to their cages. At 0, 30, 60 and 90 minutes following the *croton* oil administration, groups of four animals were anesthetized with halothane and euthanized. Cream was wiped from the ears and ears were removed and weighed.

The effects of 10 mg of a cream containing 1.0 percent RS-norketotifen at 30, 60 and 90 minutes after administration of test articles are shown in the following table 4. All results represent mean ear weights (±S.E.M.) from 8 ears.

TABLE 8

Anti-inflammatory effects *in vivo*

| Time after Croton Oil | Average Ear Weight (mg) ±S.E.M | |
|---|---|---|
| Application (min) | Vehicle | RS-Norketotifen |
| 0 (predose) | 35 ± 1 | 36 ± 1 |
| 30 | 41 ± 1 | 36 ± 1 |
| 60 | 41 ± 1 | 37 ± 2 |
| 90 | 46 ± 2 | 36 ± 2 |

In this study, the test article (racemic norketotifen) was applied topically to the ears of mice. There were obvious and potent anti-inflammatory effects after dermal application of a cream containing 1.0 percent (w/w) norketotifen.

Example 9

Antipruritic Effects In Vivo. Topical Drug Administration

Antipruritic effects were tested in vivo in CD-1 female mice aged 10-12 weeks, according to methods known in the art. The hair was clipped over the rostral part of the back at the interscapular level of the mice one day before dosing. Before testing, the mice were placed in individual clear plastic cages for at least one hour for acclimation. The animals were dosed topically by sparingly applying the formulated cream, containing 1.0% RS-norketotifen.

In preparing 1% creams, the free base of RS-norketotifen was dissolved in ethanol, resulting in a 2.5% solution. Lanolin was weighed and liquified by submerging the vessel containing lanolin in hot water. While the lanolin was liquid, it was rapidly nixed (by vortexing) with the 2.5% norketotifen solution in ethanol, resulting in in a 1.0% solution. The ethanol/lanolin solution was allowed to solidify, resulting in a cream which consisted of 1.0% RS-norketotifen in 60% lanolin/40% ethanol. A cream containing 60% lanolin/40% ethanol served as control.

Sixty minutes after the topical application of the cream, an intradermal injection of histamine (300 nmol in 20 µl phosphate buffered saline (PBS), pH 7.4) was administered into the clipped area. Immediately after the histamine injection, the bouts of scratches by the mice were counted for 40 minutes.

To date, norketotifen has been tested in one dose (cream containing 1.0% norketotifen). No reference compounds have yet been tested.

Test results obtained to date are shown in Table 9.

TABLE 9

Effects of norketotifen cream on histamine-induced pruritus in mice.

| Test Article | N | Bouts/ 40 min | Bouts as % of Vehicle Controls |
|---|---|---|---|
| Cream (vehicle) | 8 | 144 ± 16 | 100 |
| Cream w. NORK 10 mg/ml | 8 | 61 ± 4 | 42 ** |

** means P < 0.01
NORK = norketotifen

From these results, it can be concluded that a single topical application of a cream containing 1 percent RS-norketotifen reduced the histamine-induced pruritus in mice to 42% of the Vehicle Control value.

Example 10

Antimicrobial Tests of Norketotifen

Studies were performed to evaluate possible antimicrobial activities of norketotifen at various concentrations and various pHs. Norketotifen hydrogen fumarate was inoculated with standard microbial solutions at concentrations of 0.2% and 0.035% percent. The standard microbial solutions of norketotifen contained the following excipients: Sodium citrate (0.3%), propylene glycol (1.75%), methylparaben (0.03%), propylparaben (0.01%), sterile water (as diluent).

Study 1: *Staphylococcus aureus; Helicobacter pylori* and *Candida albicans*

The microorganisms were inoculated into 50 mL centrifuge tubes containing 10 mL of test sample at T=0. One (1) mL was aliquoted from each centrifuge tube for each of the following 4 weeks (except at 21 days). The log reduction was determined by the plate count method after 7, 14 and 28 days by diluting in DEB (D/E neutralizing Broth) from $10^{-1}$ to $10^{-4}$ for bacteria. Bacterial plates were poured with SCDA (Soybean Casein Digest Agar) and incubated at 32.5±2.5° C. for 3-5 days When incubated with 0.2% norketotifen, *Staphylococcus aureus* showed a reduction from 600,000 to ND (not detected) bacteria within 7 days.

When incubated with 0.035% norketotifen, *Staphylococcus aureus* showed a reduction from 750,000 to 90,000 within 7 days and to ND (not detected) within 28 days.

When incubated with 0.2% norketotifen, *Helicobacter pylori* showed a reduction from 700,000 to ND (not detected) bacteria within 7 days When incubated with 0.035% norketotifen, *Helicobacter pylori* showed a reduction from 400,000 to ND (not detected) bacteria within 7 days When incubated with 0.2% norketotifen, *Candida albicans* showed a reduction from 500,000 to ND (not detected) cells within 7 days.

When incubated with 0.035% norketotifen, *Candida albicans* showed a reduction from 500,000 to 500 cells within 7 days and to ND (not detected) within 28 days.

Studies using the single R- or S-atropisomer of norketotifen or racemic ketotifen or a single S- or R-atropisomer of ketotifen are tested and results demonstrate antimicrobial activity against *Staphylococcus aureus, Helicobacter pylori* and *Candida albicans*.

Study 2: *Malassezia* sp

The test article (norketotifen) was weighed and diluted into PBS to final concentrations of 0.210% and 0.035% before use. A 5 mL volume of the Test Article was aliquoted to a sterile 15 mL tube and the *Malassezia* sp (for example *M. pachydermatis*) were added at target concentrations of approx. $1.0 \times 10^6$ CFU/mL. The resulting mixture was vortexed thoroughly and incubated at room temperature for 7 days. A 0.500 mL aliquot of control and test tubes were harvested in 9.5 mL of D/E broth and any surviving test microorganisms were enumerated per standard dilution and plating techniques. Reductions were compared to a PBS Control at Time Zero and replicate tests were performed.

When incubated with 0.2% norketotifen *Malassezia pachydermatis* showed a reduction by 99.995% after 24 hours and ND (not detected) after 7 days When incubated with 0.035% norketotifen *Malassezia pachydermatis* showed a reduction by 99.8% after 24 hours and ND (not detected) after 7 days Other *Malassezia* sp generated similar results.

Studies using the R— or S— atropisomer of norketotifen or ketotifen and the single atropisomers thereof were also tested and preliminary results demonstrate antimicrobial activity against *Malassezia* sp.

Because norketotifen has now been found to have potent antimicrobial activity against *Streptococcus aureus, Candida albicans, Helicobacter pylori* and *Malassezia* sp, it is concluded that norketotifen will be useful therapy against said microorganisms that are known to be causative for various diseases, particularly dermal diseases. Further, since norketotifen is well-absorbed after oral administration and accumulates in high concentrations in the skin, it is concluded that oral administration of norketotifen will have therapeutic activity against various dermal diseases, such as psoriasis, atopic dermatitis and other forms of dermatitis, such as for example *Malassezia* dermatitis.

Example 11

Exemplary Oral Dosage Formulation

TABLE 10

Tablet formulations

| Ingredient | Amount per tablet | Amount per batch |
|---|---|---|
| Norketotifen | 40 mg | 400 g |
| Microcrystalline cellulose | 30 mg | 300 g |
| Lactose | 70 mg | 700 g |
| Calcium stearate | 2 mg | 20 g |
| FD & C Blue #1 Lake | 0.03 mg | 300 mg |

The active ingredient is blended with the lactose and cellulose until a uniform blend is formed. The blue lake is added and further blended. Finally, the calcium stearate is blended in, and the resulting mixture is compressed into tablets using for example a 9/32-inch (7 mm) shallow concave punch. Tablets of other strengths may be prepared by altering the ratio of active ingredient to the excipients or to the final weight of the tablet.

Those skilled in the art realize that oral formulations can also be in the form of for example a capsule, a dog-treat or a liquid formulation.

Example 12

Exemplary Topical Dosage Formulations for Mammals

Examples of topical solutions, topical ointments, topical emulsions and topical creams are shown in Tables 11-17.

TABLE 11

Examples of topical solutions formulations containing norketotifen

| Excipients in per cent | 1008 | 1009 | S1010 |
|---|---|---|---|
| Norketotifen HF (%) | 0.2 | 0.2 | 0.2 |
| Sodium phosphate dibasic | 0.473 | — | 0.160 |
| Sodium phosphate monobasic, monohydrate | 0.460 | — | — |
| NaCl | 0.480 | — | — |
| Sodium citrate | — | 0.300 | — |
| Propylene glycol | — | 1.750 | — |
| Methylcellulose | — | — | 0.500 |
| Glycerin | — | — | 2.400 |
| Water | q.s. | q.s. | q.s. |
| pH | 4.6-6.2 | 4.6-6.2 | 4.6-6.2 |

Norketotifen HF = norketotifen hydrogen fumarate

If needed, the viscosity can be adjusted by a viscosity-modifying agent to obtain the preferred viscosity. The final acidity can be adjusted by adjusting the concentrations of the buffering agents or by adding an acid or a base.

The solution formulations were prepared by adding the excipients, one at a time to an appropriate amount of water, followed by mixing until dissolved. Once all excipients had been added and dissolved, norketotifen was added to the solution of excipients and mixed continuously until dissolved. The acidity of the solutions was measured and adjusted by modifying the buffer system or by adding an acid or a base solution to the desired pH. If needed, viscosity and tonicity were adjusted as indicated.

TABLE 12

An example of hydrophilic ointments/ gels containing norketotifen

| | Batch G1009 |
|---|---|
| Norketotifen HF (%) | 1.0 |
| PEG 300 (%) | 69..0 |
| PEG 3350 (%) | 30.0 |

The solubility of norketotifen was significantly increased in certain formulations, such as gels and ointments where the solvents were not water. Thus, the solubility of norketotifen was about 1.0 percent in formulation G1009 (Table 12), where the solvent was a mixture of two polyethylene glycols.

The composition of Table 12 was prepared by mixing the two polyethylene glycols in a suitable container and heating to 60-65° C. This heating step melts the high molecular weight polyethylene glycol. Next, norketotifen was added and the composition was mixed until the active ingredient was dissolved. Finally, the composition was cooled with mixing to allow the ointment/gel to thicken. The viscosity was 30,000 cP or greater. The pH range for these compositions was not measured since the formulations were non-aqueous. If needed, the tonicity can be adjusted by adding a tonicity-adjusting agent to obtain the preferred tonicity.

TABLE 13

An example of hydrophobic ointments/ gels containing norketotifen

| | Batch G1012 |
|---|---|
| Norketotifen HF (%) | 1.0 |
| Propylene glycol (%) | 10.0 |
| Glyceryl stearate (%) | 0.5 |
| Cetyl alcohol (%) | 0.5 |
| White petrolatum | q.s.(2) |

Batch G1012 contained propylene glycol as a solvent for norketotifen, glycerol stearate and cetyl alcohol as surfactants and white petrolatum as base.

The hydrophobic ointment was prepared by dissolving norketotifen in propylene glycol. The solubility of norketotifen was about 1.0 percent in propylene glycol. Next, glyceryl stearate, cetyl alcohol, and white petrolatum were added to a suitable container and heated to 65-70° C. This heating step melts the surfactants and the petrolatum. Next, norketotifen solution was slowly added and the composition mixed until the solvent was dispersed. Finally, the composition was cooled with mixing to allow the ointment to thicken.

If needed, acidity can be adjusted by adding an acid solution or a base solution to obtain the preferred acidity. If needed, viscosity can be adjusted by a viscosity-modifying agent to obtain the preferred viscosity.

TABLE 14

Examples of topical emulsions containing norketotifen

| | ED1012b | ED1015b |
|---|---|---|
| Norketotifen HF (%) | 1.0 | 1.0 |
| Sodium phosphate dibasic (%) | 0.160 | 0.160 |
| Propylene glycol (%) | 1.850 | 1.850 |
| Castor oil (%) | 1.250 | 1.250 |
| Polyoxyl 35 castor oil (%) | 1.000 | 1.000 |
| Methylcellulose (%) | 0.200 | — |
| 1.0 N HCl or 1.0 N NaOH (%) | q.s. to target pH | q.s. to target pH |
| Water | q.s. (2) | q.s. (2) |
| pH | 5 to 7 | 5 to 7 |

The batches ED1012b and ED1015b contained a phosphate buffer, propylene glycol as solvent/moisturizer/tonicity modifier, parabens as preservatives, castor oil and polyoxyl castor oil as surfactants and methylcellulose (if used) as a stabilizer/viscosity modifier. Emulsions containing norketotifen can be used at pH of about 5.0 to about 7.0.

The selected emulsions in Table 14 were prepared by adding propylene glycol, castor oil, ethoxylated castor oil, and water to a suitable container. The contents of the container were sonicated with a ½" ultrasonic probe (Sonics Inc. Vibra Cell) for 20 minutes. The resulting emulsion droplets were mostly less than 0.5 microns. The emulsion was filtered through a 0.22-micron cellulose acetate filter. After filtration, norketotifen and buffer salts were added.

The viscosity of norketotifen emulsions can be adjusted by a compatible viscosity-modifying agent.

TABLE 15

An example of liposome
compositions containing norketotifen

|  | LIP1011 |
| --- | --- |
| Norketotifen HF (%) | 1.0 |
| Sodium phosphate dibasic (%) | 0.16 |
| Glycerin (%) | 2.40 |
| Soy lecithin (%) | 1.00 |
| Cholesterol (%) | 0.05 |
| Water | q.s. |

Topical liposome compositions were made, comprising norketotifen at concentrations preferably between 0.01 percent and 1.0 percent. The liposome compositions were having a preferred viscosity that ranged from 1.000 to 200,000 cP. Topical liposome compositions have pH of 4 to 7, preferably pH 5.2 to 6.2. The liposome compositions are approximately isoosmotic. Said emulsions also contained excipients, such as humectants, viscosity modifying agents, tonicity agents, chelating agents, buffers, surfactants, mucoadhesives and antioxidants. Said liposome emulsions were designed for once-daily dermal administration or for repeated dermal administrations from two to five times daily to a mammal in need thereof.

Incorporating norketotifen in a selected liposome composition will enhance residence time in the skin and improve drug delivery to the tissues. An exemplary liposome composition containing norketotifen is shown in Table 16. The acidity can be changed by adjustment of the buffer or by adding an acid or a base as known to those skilled in the art.

TABLE 16

An example of a dermal
suspension containing norketotifen

|  | SUS1011 |
| --- | --- |
| Norketotifen FB (%) | 5.0 |
| Poloxamer 407 | 0.6 |
| Boric acid | 0.2 |
| Sodium chloride | 0.2 |
| Water | q.s. |
| pH | 5.0 to 7.0 |

NorketotifenFB = norketotifen free base

Both norketotifen HF and norketotifen FB can be formulated as suspensions. Several experiments were done and acidity was adjusted over a wide range. It was determined that emulsions can be used at pH of about 5.0 to about 7.0. An example of a preferred suspension containing norketotifen free base is shown in Table 9F, where all percent are w/w.

Viscosity will be adjusted by addition of one or more viscosity-modifying agents, which will offer stability to the suspensions.

TABLE 17

An example of a dermal
cream containing norketotifen

|  | PT 112706 |
| --- | --- |
| Norketotifen FB (%) | 1.0 |
| Ethanol (%) | 39.0 |
| Lanolin (%) | 60.0 |
| Surfactant(s) (%) | (0.2) |
| Antioxidant(s) (%) | (0.2) |

Both norketotifen salts and norketotifen free base can be formulated as creams. An example of a cream containing norketotifen free base is shown in Table 17, where all percent are w/w.

In preparing creams containing 1 percent of the free base of norketotifen, the active ingredient was dissolved in ethanol, resulting in a 2.5 percent solution. Lanolin was weighed and liquefied by submerging the vessel containing lanolin in hot water. While the lanolin was a liquid, it was rapidly mixed (by vortexing) with the 2.5% norketotifen solution in ethanol to result in a 1.0 solution. The ethanol/lanolin solution was allowed to cool off and solidify, resulting in a cream which consisted of 1 percent norketotifen in the lanolin/ethanol cream, which will be kept in a closed tube to avoid evaporation. To improve shelf-life, a surfactant (such as for example glyceryl stearate, 0.1 to 0.3 percent) and an antioxidant (such as for example ascorbic acid, 0.1 to 0.3 percent) can optionally be added, as shown in Table 17.

Dosage forms for topical (dermal) application may be prepared for example as solutions (Table 11), as hydrophilic ointments (Table 12), as hydrophobic ointments (Table 13), as emulsions (Table 14), as liposome compositions (Table 15), as suspensions (Table 16), and as creams (Table 17). The dermal compositions may also contain additional excipients, and a large number of excipients have been tested for compatibility with norketotifen. Dermal composition may contain one or more active compounds and the compounds may be prepared as bases or salts. Dermal composition may be applied to the skin under occlusive dressing or as a constituent of a dermal delivery system ("patch," etc.)

As used herein, the terms "pharmaceutically acceptable salts" or "a pharmaceutically acceptable salt thereof" refer to norketotifen salts, which have been prepared from pharmaceutically acceptable non-toxic acids. Exemplary pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrochloride salt and the hydrogen fumarate salt are particularly preferred.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treating skin infections in a dog or cat, comprising administering to the dog or cat with a skin infection a topical formulation comprising a therapeutically effective amount of norketotifen or a salt or isomer thereof and a pharmaceutically acceptable excipient, wherein the skin infection is a fungal infection caused by *Malassezia pachydermatis* or *Candida albicans*, or a bacterial infection caused by *Staphylococcus aureus*.

2. The method of claim 1, wherein the topical formulation is administered to an infected skin lesion and/or infected areas adjacent to the skin lesion on the dog or cat.

3. The method of claim 1, wherein the dog or cat has atopic dermatitis.

4. The method of claim 1, further comprising orally administering a composition comprising RS-norketotifen and a pharmaceutically acceptable excipient.

5. The method of claim 1, wherein the skin infection is a hot spot.

6. The method of claim 1, wherein the topical formulation contains norketotifen or the salt or isomer thereof at a concentration of 0.01 percent to 20.0 percent by weight.

* * * * *